(12) United States Patent
Dietz et al.

(10) Patent No.: US 6,358,501 B1
(45) Date of Patent: Mar. 19, 2002

(54) POLYPEPTIDE-POLYSILOXANE COPOLYMERS

(75) Inventors: Thomas Dietz, Essen; Peter Lersch, Oberhausen; Christian Weitemeyer, Essen, all of (DE)

(73) Assignee: Goldschmidt GmbH, Essen (DE)

( * ) Notice: Subject to any disclaimer, the term of this patent is extended or adjusted under 35 U.S.C. 154(b) by 0 days.

(21) Appl. No.: 09/419,144

(22) Filed: Oct. 15, 1999

(30) Foreign Application Priority Data

Oct. 17, 1998 (DE) .......................................... 198 48 002

(51) Int. Cl.⁷ .............................. A61K 7/06; A61K 7/11
(52) U.S. Cl. ................. 424/70.12; 424/78.37; 424/78.1; 528/26; 528/28
(58) Field of Search ................. 528/26, 28; 424/70.12, 424/78.37

(56) References Cited

U.S. PATENT DOCUMENTS

| | | |
|---|---|---|
| 3,562,353 A | 2/1971 | Chow et al. |
| 4,534,881 A | 8/1985 | Sikes et al. |
| 4,925,673 A | 5/1990 | Steiner et al. |
| 4,963,364 A | 10/1990 | Fox et al. |
| 4,996,292 A | 2/1991 | Fox et al. |
| 5,100,956 A | 3/1992 | O'Lenick, Jr. |
| 5,243,028 A | 9/1993 | O'Lenick, Jr. |
| 5,373,085 A | 12/1994 | Fox et al. |
| 5,516,869 A * | 5/1996 | Garelli et al. ............. 528/26 |
| 5,753,214 A * | 5/1998 | Yoshioka et al. ........ 424/70.2 |

FOREIGN PATENT DOCUMENTS

EP    0 540 357 A2    5/1993
EP    0 699 431 A1    3/1996

OTHER PUBLICATIONS

Kania et al., "Preparation of Poly(dimethylsiloxane)–Polypeptide Block Computer", Journal of Applied Polymer Science, vol. 27, pp. 139–148, 1982.

Bahn et al., "Thermal proteins +", Chemtech, May 1996, pp. 26–29.

Derwent Abstract, 93–096828/12, abstract of JP 05–39359 (1993).

Derwent Abstract, 95–332458/43, abstract of JP 07–228508 (1995).

* cited by examiner

*Primary Examiner*—Thurman K. Page
*Assistant Examiner*—Liliana Di Nola-Baron
(74) *Attorney, Agent, or Firm*—Frommer Lawrence & Haug LLP

(57) ABSTRACT

The present invention relates to polypeptide-polysiloxane copolymers, to their preparation by thermal copolymerization of amino acids with organofunctional polysiloxanes, and to their use as interface-active substances. The polypeptide-polysiloxane copolymers consist of at least one polysiloxane unit

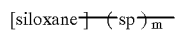

and of at least one polypeptide unit

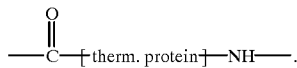

17 Claims, No Drawings

POLYPEPTIDE-POLYSILOXANE COPOLYMERS

RELATED APPLICATIONS

This application claims priority to German application No 198 48 002.4, filed Oct. 17, 1998, herein incorporated by reference.

BACKGROUND OF THE INVENTION

1. Field of the Invention

The present invention relates to polypeptide-polysiloxane copolymers, to their preparation by thermal copolymerization of amino acids with organofunctional polysiloxanes, and to their use as interface-active substances.

2. Description of the Art

Proteins are naturally occurring polypeptides and play an important role in all biological processes. They are being used increasingly in personal care products as conditioners, humectants and emollients. Proteins are natural, high molecular weight polymers and are generally hydrolyzed to low molecular weight proteins so that they are soluble in water. Although protein hydrolyzates can be incorporated more easily into formulations, the soluble proteins are less substantive on skin and hair.

Silicone is the collective term for a large number of compounds with varying properties, but which are all characterized by the silicon-oxygen bond in the siloxane chain. Like proteins, they likewise play an important role in personal care, in particular as conditioners. Polydimethylsiloxanes, for example, are substantive on skin and hair, make hair shiny and smooth and produce a pleasantly soft and silky feel on the skin. However, they are virtually insoluble in water. Although silicone polyethers are water-soluble silicone derivatives which are able to make the hair smooth, they are not very substantive.

Proteins and silicones are thus two very different classes of substances having likewise different properties and advantages which are useful in each case for cosmetic applications. The development of proteins, which also have some of the characteristic properties of silicones such as the smoothing of hair and skin, or of silicones, which have the advantages of proteins such as better solubility in water and higher substantivity, has given access to products with properties which cannot be obtained by simple mixtures of the two classes of substances.

U.S. Pat. No. 3,562,353 has already described the combination of silicones with polypeptides in the form of copolymers. These are block copolymers of the ABA or (AB)n type, which are obtained by coupling end-functionalized homopolymers. A is a polyamide moiety having a molecular mass of from 2,000 to 100,000 and B is a silicone moiety having a molecular mass of from 500 to 100,000. The compounds are thermoplastic block copolymers which are either elastic or solid and can be used as biocompatible implant materials. They are prepared by the reaction of a polyamide consisting of alpha-amino acids and having reactive end groups such as hydroxyalkyl, aminoalkyl or isocyanato groups with a silicone which carries reactive end groups such as chloroalkyl, carboxyl, isocyanato, hydroxyalkyl or aminoalkyl groups. However, the functional polyamide must first be prepared with additional synthetic expenditure including protection-group chemistry. In a first stage, the corresponding N-carboxyanhydride is prepared from the alpha-amino acid by reaction with phosgene in a solvent such as dioxane. If the alpha-amino acid is a dicarboxylic acid such as glutamic acid or aspartic acid, then one carboxyl group must first be esterified by esterification, for example, with an excess of benzyl alcohol in the presence of hydrobromic acid. If it is an alpha-amino acid containing another amino, hydroxyl or mercapto group, these must then likewise be protected in a suitable manner prior to the reaction with phosgene in order to avoid undesired side reactions. In a second stage, the protected alpha-amino acid is then reacted to give the polyamide. This multistage synthesis may be illustrated more detailed by means of the following example Starting from the N-carboxyanhydride, protected in the form of the benzyl, ester, of L-glutamic acid, N-carboxy-gamma-benzyl L-glutamate is prepared. Then this is polymerized with ethanolamine as initiator in dimethylformamide as solvent. After about 90% conversion, the N-carboxyanhydride of phenylalanine must be added so that it forms the end group of the polyamide. The polymer formed must be precipitated in water and washed with methanol. In the next step, the polyamide is heated in epsilon-caprolactone as reagent and solvent for over 50 h (!), then precipitated again in water and washed with methanol. This gives a polyamide which carries hydroxyalkyl groups at both ends. The dihydroxy-functional polyamide is then reacted in a mixture of benzene and dichlorobenzene as solvent with alpha, omega-bis (dimethylamino)poly(dimethylsiloxane) with the elimination of dimethylamine. The polymer is precipitated out with methanol and washed with hexane. Thus, to prepare the copolymers described in U.S. Pat. No. 3,562,353, a large number of reaction and work-up steps are required, including complex protection-group chemistry. In addition, some of the reagents required are very toxic, such as phosgene, and the reactions are carried out in solvents such as benzene and dimethylformamide, from which the product must be recovered. As a rule, the polypeptide moiety contains amino acids containing protective groups, such as benzylglutamic acid and nonpolar amino acids such as phenylalanine. The copolymers are thus virtually insoluble in water. On the other hand, the linking between polyamide and silicone moiety is carried out via a hydrolysis-sensitive Si—O—C bond, meaning that if the protective groups were removed, the bond between silicone and peptide moieties would be cleaved again and additionally degradation reactions on the polysiloxane would be triggered Journal of Applied Polymer Science, 27, 1982, 139–148 likewise describes the preparation of polypeptide-polysiloxane block copolymers. These are obtained by polymerization of the N-carboxyanhydrides of phenylalanine and gamma-benzylglutamic acid with an alpha, omega-aminopropyl-functional polydimethylsiloxane as initiator. The resulting block copolymers are white, soft solids. However, as in U.S. Pat. No. 3,562,353, the preparation of the copolymers requires a large number of reaction and work-up steps, as well as protective groups and solvents. A typical reaction time for the polymerization is in the range between 100 and 200 h (!).

U.S. Pat. No. 5,100,956 claims silicone-protein copolymers in which the silicone moiety is linked to the amino group of a protein via a polyether phosphate group. Although the polyether phosphate unit makes the polymers soluble in water, they also have a very hydrolysis-sensitive phosphoric ester function, meaning that the silicone and protein moieties can again be readily cleaved from one another. In addition, it must be accepted that the polyether residues, which act as spacers and linking element between protein and silicone moieties, because of their polymer distribution and the high molecular weight character associated therewith, do not leave the properties of the product unaffected and have the property profile of hybrid silicone-polyether protein copolymers rather than act as pure silicone-protein copolymers. The silicone-protein copolymers are prepared by reacting water-soluble epoxy-functional polysil(ox)anes with hydrolyzates of natural proteins in water. The solubility of the polysiloxanes in water is here achieved by hydrosilylating addition reaction of polyethers and subsequent phosphatation of the hydroxyl group. An epoxy group, which is able to react with free amino groups of the protein, is then introduced into the silicone by reaction of the sodium salt of the silicone phosphate with epichlorohydrin. Thus synthesis route also has several stages and uses hazardous and highly toxic reagents such as phosphorus pentoxide or epichlorohydrin.

Another U.S. Patent U.S. Pat. No. 5,243,028, also describes an improved process variant for the preparation of silicone-protein copolymers. This involves firstly reacting a hydroxy-functional silicone polyether with chloroacetic acid to give the corresponding chloroacetate-functional siloxane. This is then followed by the reaction with proteins or protein hydrolyzates under defined conditions, where, within the scope of a substitution reaction, the organically bonded chlorine is converted into the chloride form and linking to the protein takes place. Although this process is an overall improvement, it is not possible to refrain from the use of caustic and toxic chloroacetic acid here either. It is a further disadvantage that the linking between silicone residues and the protein radical takes place via an ester group which is not stable to hydrolysis. This severely limits the use of such materials in aqueous formulations and even makes long-term storage under aqueous conditions impossible. Furthermore, it has to be feared that such products, because of the hygroscopic properties of the protein radical, are themselves not insufficiently stable in solid form and that, as the storage time increases, an increase of a retro-cleavage to the silicone polyether and free protein will take place. If, as described in the examples, silicone polyethers are used as starting materials, the products are not true silicone proteins here either, but have significant hybrid character.

EP-A-0 540 357 (Croda, GB 9 123 251, November 1991) claims protein-silicone copolymers in which the silicone component is covalently bonded to the amino groups of the protein. In each case at least some of the silicone components contribute to the crosslinking between various protein chains, but additionally noncrosslinking siloxane units may also be present. Serving as protein component are natural proteins such as collagen, elastin etc., which have either been partially hydrolyzed or have been modified by chemical modification such as esterification or quatemization. The copolymers are formed by reaction of functional groups of silanes or silicones with the amino groups of the protein. This produces higher molecular weight polymers which also contain protein chains crosslinked with one another. Additional crosslinking can take place as a result of the condensation of silanol groups of the silanes or silicones. An important requirement for the reaction of the protein component is its solubility in water or another suitable solvent such as ethanol or propylene glycol or in mixtures thereof. Another prerequisite is the ability of the silicone component to effect crosslinking with the protein component. Required for this purpose are either polyfunctional silicones with suitable reactive groups such as acid halide, anhydride or epoxide groups, or monofunctional silicon compounds which contain silanol groups or groups which can form silanol groups by hydrolysis in situ, which cause crosslinking as a result of condensation to siloxane bonds. In order for the silicon compound to react with the protein, it must be soluble in the same solvent as the protein, which is preferably an aqueous protein hydrolyzate. Therefore, if water is solvent, an organofunctional silane with hydrolyzable groups is required. Here, the reaction conditions must be controlled very carefully. This is because first a pH above 7 is usually required so that the amino groups of the protein are reactive, and, second, rapid hydrolysis of the cleavable groups usually takes place under alkaline conditions. However, at the same time, a condensation of the silane takes place, meaning that the overall reaction can be controlled only with difficulty. This method, therefore, gives only crosslinked products. Since such products do not contain linear polydimethylsiloxane segments, their typical silicone properties are not very pronounced either. In addition, the products can be handled only in the form of aqueous solutions since a solid, water-insoluble film forms as soon as the water is removed by distillation or drying. The reaction can, for example, be carried out in ethanol so that organofunctional dimethylsilicones, which are insoluble in water, but soluble in ethanol at least in small amounts, can be used. However, it is necessary to use the ethyl ester of the protein hydrolyzate, which again involves additional reaction steps. In addition, the pH required for the reaction is adjusted using sodium hydroxide, which, at reaction temperatures around 70° C., can cause undesired siloxane chain degradation. It is stated that the chemical structure of the protein-silicone copolymers is very complex and it is therefore impossible to assign to them an individual general structural formula.

EP-A-0 699 431 claims silylated peptides in which the amino group of a peptide carries only one silyl group. The linking between silicon compound and peptide is produced in a similar manner to EP-A-0 540 357 by reaction of the amino groups of the peptide with a reactive group of the silicon compound. The silicon compound used is a silane with a haloalkyl group. In order that the hydrophilic peptides can react with the hydrophobic silyl compounds in water, the other groups of the silane must first be hydrolyzed so that the silane becomes soluble in water. When haloalkylsilanes are used, a hydrohalic acid forms, which lowers the pH of the reaction mixture. For this reason, the pH of the reaction mixture must be kept constant by addition of sodium hydroxide so that the reaction of the halogen group with water is avoided. In order that at least two silyl groups can be introduced per peptide, the peptide must contain amino acids with an additional amino group, as is the case with lysine. The silicon content is thus only inserted in the form of silyl groups and, more specifically, of only one silyl group per amino group of the protein. For this reason, as in EP-A-0 540 357, a dimethylsilicon effect is not to be expected in the case of the silane-based protein-silicone copolymers either.

Natural proteins and synthetic peptides are linear polymers of amino acids which are linked together via an amide bond (peptide bond). However, when an amino acid is heated to above 100° C., a polymer is not usually obtained. Rather, a rapid black discoloration is observed, which can be attributed inter alia to the formation of heterocycles. Exceptions to this are aspartic acid, which forms polysuccinimide upon heating, which can be converted into polyaspartic acid under basic conditions. Glutamic acid cyclizes upon heating to give monomeric pyroglutamic acid (2-pyrrolidone-5-carboxylic acid). In the early 1950s, Fox and Middlebrook (Chemtech, May 1996, p. 26–29) discovered that heating glutamic acid and aspartic acid gives a copolymer of the two amino acids. Further, other amino acids, which are unable to form polymers on their own, can be reacted with glutamic acid and/or aspartic acid to give copolymers. A feature of these "thermal proteins" or "protenoids" is that they have nonrandom distribution in the amino acid sequence. This observation has led to the development of a unique research direction which is based on the origin of life based on proteins which can be obtained under terrestrial conditions. Thermal proteins have a molecular mass of up to 9000, which is low compared with natural proteins, and are therefore nontoxic and thus biocompatible with living systems. They are used, for example, in the microencapsulation of pharmaceuticals (U.S. Pat. Nos. 4,963,364, 4,925,673), as artificial skin (U.S. Pat. No. 4,996,292) or as active ingredient for improving memory performance (U.S. Pat. No. 5,373,085). The industrial use as inhibitors of mineral deposition in cooling-water systems is also described (U.S. Pat. No. 4,534,881). A further important advantage is their biodegradability.

The discussion of the prior art shows that silicone-protein copolymers are known, but that they hitherto have serious disadvantages. Either the copolymers are insoluble in water because the peptide component contains amino acid units carrying protective groups, or they are soluble in water, but then have a bond between peptide and silicone moiety which is sensitive to hydrolysis. The known processes for the preparation of such silicone-protein copolymers also have considerable disadvantages. They are either complex, multistage preparation processes in which toxic substances are often required, or are simple processes such as the silylation of peptides. The products cannot, however, be expected to have a true silicone effect.

OBJECT OF THE INVENTION

An object of the invention, then, was to find new types of silicone-peptide copolymers which are soluble in water and at the same time are highly molecular and thus substantive. In addition, they should contain relatively long poly (dimethylsiloxy) units and thus exhibit a significant silicone effect. An other object was to find a process which is easy to carry out and does not require toxic reagents. These and other objective will become apparent to the practioner upon reading the specification.

SUMMARY OF THE INVENTION

Surprisingly, it has now been found that thermal copolymerization of natural and unprotected amino acids, in particular aspartic acid and glutamic acid with organofunctional polysiloxanes, give polypeptide-polysiloxane copolymers which could be converted into a water-soluble form and display a true silicone effect.

The chemical combination of such thermal proteins with silicones to give silicone-protein copolymers is not known. Surprisingly, it has been found that, despite the drastic reaction conditions, such as temperatures of above 170° C. in a pH-acidic amino acid melt, reactive organopolysiloxane can be incorporated into the peptide with retention of the dimethylsilicone chains during the thermal polymerization of, in particular, aspartic acid and glutamic acid and other amino acids.

The invention thus provides new types of polypeptide-polysiloxane copolymers, processes for their preparation and their use as interface-active substances.

DESCRIPTION OF THE PREFERRED EMBODIMENTS

The present invention provides, in a first embodiment, polypeptide-polysiloxane copolymers consisting of at least one polysiloxane unit

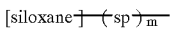

where the index m is a positive integer in the range m=1–52, of the general average formula I:

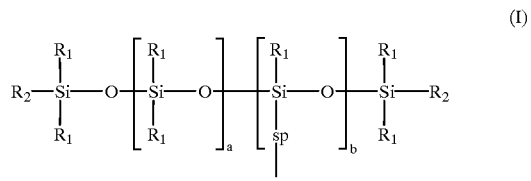

where
  $R_1$=alkyl radical, preferably having from 1 to 4 carbon atoms,
  $R_2$=$R_1$ and/or -sp-
where
  -Sp-=divalent spacer between siloxane and another functional group, silicon atom and spacer being linked via a silicon-carbon bond, in particular a divalent alkylene radical having, preferably, from 1 to 20 carbon atoms, which is optionally branched, and may contain double bonds or aromatic rings, and heteroatoms, in particular oxygen, nitrogen or sulfur,
  the indices a and b are integers in the ranges a=0–200 and b=0–50,
  with the proviso that when a=b=0 and when b=0 and a≠0, at least one $R_2$=-sp- in each case,
and of at least one polypeptide unit

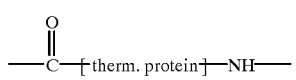

where
  therm. protein is a structure of the general average formula II:

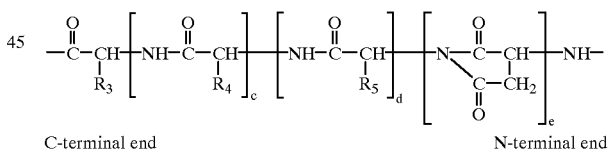

C-terminal end                                      N-terminal end or of the formula III:

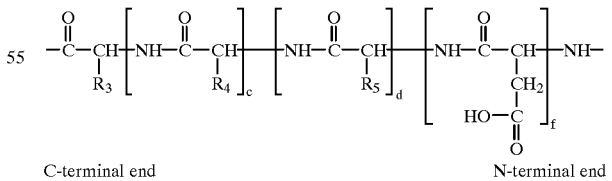

C-terminal end                                      N-terminal end which is linked to the polysiloxane unit via a divalent functional group

-FGeither via the C-terminal end, the N-terminal end or both ends of the polypeptide unit, and is a structural unit —CH(OH)CH$_2$— or —CH(OH)CH$_2$O—, —CO—, —CH(CH$_2$CO$_2$H)CO—, —NH—, —O—, —S—, —CH(NH$_2$)CO— or —CH(CO$_2$H)NH—
and optionally additional links between polysiloxane and polypeptide units result via the radicals R$_4$ and/or R$_5$
where
R$_3$=R$_4$ or R$_5$,
where
R$_4$=is identical to a radical of an amino acid and —(CH$_2$)$_4$—NH—R$_6$,
where
R$_6$=H (lysine) or

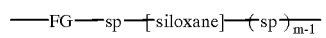

R$_5$=—CH$_2$—CH$_2$—CO—R$_6$
where
R$_6$=OH (glutamic acid) or

c, d, e and f are positive integers including 0, with the proviso that
the indices c, d, e in formula II and c, d and f in formula III are not all 0,
in particular e≠0, when c=0,
c and d≠0, when e or f=0, and
the molecular mass of the polypeptide unit is between about 250 and about 9000 and the weight ratio of polysiloxane units and polypeptide units in the polypeptide-polysiloxane copolymer is between about 1:99 and about 99:1.

Particularly preferred polypeptide-polysiloxane copolymers are those wherein:
R$_1$ is CH$_3$, m=2–32, a=8–10, b=0–30
Where, when b=0, both radicals R$_2$ then correspond to -sp-;
m=2–7, a=8–40, b=0–15, where when b=0, both radicals R$_2$ then correspond to -sp-;
c, d, and e in formula II or c, d and f in formula III do not equal 0 and the weight ratio of the polysiloxane units an the polypeptide units in the polypeptide-polysiloxane copolymer is between about 5:95 an about 55:45;
c in formula II or formula III=0 and d and e in formula II or d and f in formula III≠0
and R$_3$=R$_5$ or —CH$_2$—CO—R$_6$
where
R$_6$ is OH (aspartic acid) or

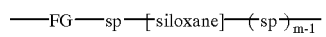

and the weight ratio of polysiloxane units and polypeptide units in the polypeptide-polysiloxane copolymer is between about 5:95 and about 55:45.
c and d in formula II or formula III=0, and e or f in formula II or formula III≠0
and R$_3$=—CH$_2$—CO—R$_6$
where
R$_6$ is OH (aspartic acid) or

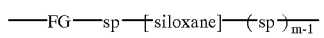

and the weight ratio of polysiloxane units and polypeptide units in the polypeptide-polysiloxane copolymer is between about 5:95 and about 55:45.

-sp- is selected from the group consisting of:
—(CH$_2$)$_3$—, —(CH$_2$)$_3$—O—CH$_2$— and —(CH$_2$)$_3$—NH—(CH$_2$)$_2$— and
-FG- is selected from the group consisting of:
—CH(OH)CH$_2$— or —CH(OH)CH$_2$O—, —CO—, —CH(CH$_2$CO$_2$H)CO—, —NH—, —O—, —S—, —CH(NH$_2$)CO— or —CH(CO$_2$H)NH—.

Polypeptide-polysiloxane copolymers which are especially particularly preferred and are those wherein the amino acids is selected for example, from the group consisting of glycine alanine, valine, leucine, isoleucine, phenylalanine, proline, serine, threonine, tyrosine, asparagine, glutamine, arginine, tryptophan, histidine, cysteine, methionine, aspartic acid and glutamic acid.

Preferred examples of compounds according to the invention are:

A)

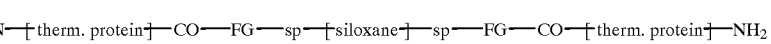

in which

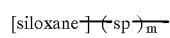

(m=2) is identical to a polysiloxane unit of the following structure:

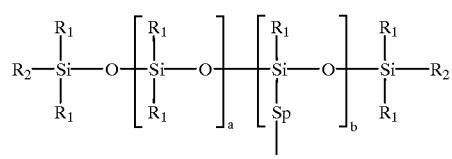

where
R$_1$=CH$_3$
both R$_2$=-sp-
sp=—(CH$_2$)$_3$—,
a=8
b=0
and

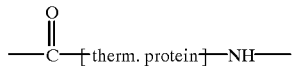

is identical to a polypeptide unit of the following structure:

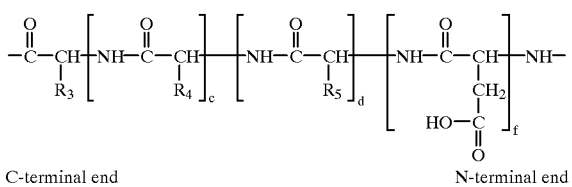

C-terminal end                                            N-terminal end where
  $R_3$=—$CH_2CO_2H$ or $(CH_2)_2CO_2H$
  c=0
  d and f≠0, and the ratio d:f is approximately 1:6,
  FG=—NH—,
the molecular mass of the polypeptide unit is about 500 and the weight ratio of polysiloxane to polypeptide units in the copolymer is 1:9.

B)

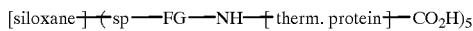

where the polysiloxane and the polypeptide units correspond to the structures given in Example A), where
  $R_1$=$CH_3$
  $R_2R_1$
  -sp-=—$(CH_2)_3$—O—$CH_2$—
  a=20
  b=5
and
where
  $R_3$=—$CH_2CO_2H$ or —$(CH_2)_2CO_2H$
  c=0
  d and f≠0, and the ratio d:f is approximately 1:6,
  FG=—CH(OH)$CH_2$—,
the molecular mass of the polypeptide unit is about 2000 and the weight ratio of polysiloxane to polypeptide units in the copolymer is 3:7.

C)

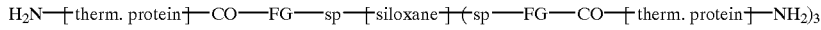

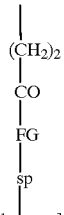

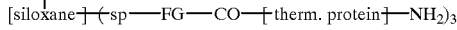

where polysiloxane and polypeptide units correspond to the structures given in Example A),
  where
  $R_1$=$CH_3$
  both $R_2$=-sp-
  -sp-=—$(CH_2)_3$—,
  a=40
  b=2 and
where
  $R_3$=—$CH_2CO_2H$ or —$(CH_2)_2CO_2H$
  c≠0 and $R_4$=—$CH_2SH$ (cysteine)
  d and f≠0, and the ratio d:f is approximately 1:4,
  FG=—NH—,
  the weight ratio of cysteine on the polypeptide moiety is about 5%,
  the molecular mass of the polypeptide unit is about 1500 and the weight ratio of polysiloxane to polypeptide units in the copolymer is 4:6.

D)

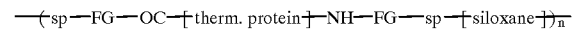

where the polysiloxane unit corresponds to the structure given in Example A), where
  $R_1$=$CH_3$
  both $R_2$=-sp-
  -sp-=—$(CH_2)_3$—O—$CH_2$—CH(OH)—$CH_2$—NH—$(CH_2)_4$—
  a=18
  b=0
and the polypeptide unit corresponds to the following structure:

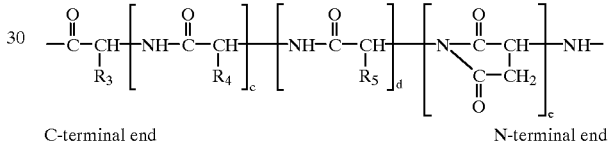

C-terminal end                                            N-terminal end where
  $R_3$=—$CH_2CO_2H$
  c and d=0
  e≠0
  FG=—CH($NH_2$)CO— or —CH($CO_2H$)NH —,
the molecular mass of the polypeptide unit is about 1000 and the weight ratio of polysiloxane to polypeptide units in the copolymer is 1:9.

A feature of this new class of compound according to the invention is that they can be obtained in a simple process and without using protective groups or solvents. A particular advantage is that the starting materials are defined compounds, namely (natural) amino acids and organically modified polysiloxanes. This is in contrast to those processes which start from protein hydrolysates, which can differ greatly from one another depending on the source of the protein (animal or vegetable), preparation process (pH, reaction temperature, reaction time) and the storage time of the solution. Reproducibility of the product quality can thus be ensured only with difficulties.

Another important advantage of the present class of compound is that their surface-active properties can be adjusted in a targeted, tailored and reproducible manner. This is achieved in a simple manner through the choice of the starting compounds and their weight ratio. Through the choice of the weight ratio of amino acids to polysiloxane, usually between about 95:5 and about 40:60, the proportion of polydimethylsiloxane units is essentially predetermined, which will affect the surface-active properties. Another parameter is the structure of the polysiloxane. It is obvious that the arrangement and the number of functional groups in the polysiloxane has a big effect on the properties of the copolymer. The siloxane can carry functional groups on both ends of the chain or in side positions in varying number. It makes a difference to the product properties what chain length, for example, a terminal-functionalized polysiloxane has or what chain length and how many functional groups per chain a comb-like polysiloxane have. Another way of modifying the surface-active properties is the nature and ratio of amino acids used to one another. Thus, for example, the addition of hydrophobic amino acids such as phenylalanine can reduce the hydrophilicty of the polypeptide moiety. In addition, the molecular weight of the copolymer can be adjusted by the way in which the reaction is carried out, in particular by the temperature and the duration of heating.

An additional important feature, is that, in contrast to the protein-polysiloxane copolymers known from the literature, the inventive compounds comprise poly(dimethylsiloxy) chains which, as a hydrophobic moiety together with the hydrophilic polypeptide moiety, form a surfactant as a result of a real chemical bond, and, therefore, a true silicone effect is achieved. Another advantage is that the copolymers, depending on the type of work-up, can be obtained in a water-insoluble or a water-soluble form. In the water-insoluble form they can, for example, be incorporated into nonpolar media. They can, however, also be obtained in a water-soluble form as aqueous solutions or, after removal of the water, in solid form. They form a dry, readily flowable powder, which mixes with water in any ratio to form clear solutions. It can be recovered again from the solutions by distilling off the water. It thus differs considerably from protein hydrolyzate organosilane or organosiloxane solutions as described in EP-A-0 540 357, which, after removal of the water, form a hard film which no longer dissolves in water.

The present invention further provides for a process for the preparation of the above-described polypeptide-polysiloxane copolymers by thermal polymerization of amino acids of the general formula:

where $R_7$ is identical or different and is the residue of an amino acid such as in glycine, alanine, valine, leucine, isoleucine, phenylalanine, proline, serine, threonine, tyrosine, asparagine, glutamine, arginine, lysine, tryptophan, histidine, cysteine, methionine, aspartic acid, glutamic acid, in the presence of organopolysiloxanes having reactive groups—RG in the formula (I) defined above.

The organopolysiloxanes to be used are known from the prior art and are available commercially or can be prepared readily in a known manner. Terminally epoxy- or amino-functionalized polysiloxanes are obtained, for example, by hydrosilylation of allyl glycidyl ethers or allylamine to a terminally functionalized hydridosiloxane. Comb-like aminopropylsiloxanes are prepared, for example, by condensation and alkaline equilibration of aminopropyldialkoxysilanes and cyclic siloxanes.

Examples of suitable organofunctional polysiloxanes are:

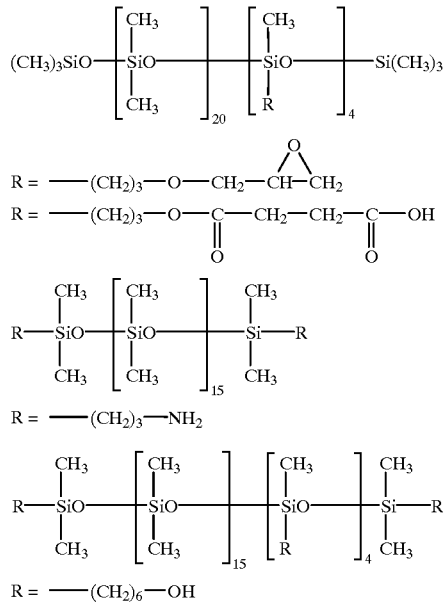

The preparation process is described below by way of example. In a first stage, glutamic acid, for example, is melted at about 170–180° C., under which the cyclic amide, pyroglutamic acid (2-pyrrolidone-5-carboxylic acid) is formed by elimination of water. Instead of glutamic acid, it is also possible to use proline or a polar, high-boiling solvent such as N-methylpyrrolidone or sulfolane. Aspartic acid is then added, and the melt or the high-boiling solution is heated at 160–220° C. In this process polysuccinimide forms, which, in cases where glutamic acid is used, also contains glutamic acid units. The duration and temperature of heating is used to control the molecular mass of the growing polymer. The longer the heating time and the higher the temperature, the higher the molecular mass. In the next step, the organofunctional polysiloxane is added dropwise. The heating time after all of the polysiloxane has been added in turn influences the molecular mass of the copolymer formed. The melt is poured out and, after cooling, forms a glasslike mass, which can be readily pulverized by grinding. This is the water-insoluble form of the polypeptide-polysiloxane copolymer.

The water-soluble form of the polypeptide-polysiloxane copolymer is obtained by treating the copolymer with alkaline aqueous solution, for example with aqueous sodium hydroxide solution. If, during this procedure, the neutral point is exceeded, then aqueous hydrochloric acid can, for example, be used for neutralization. The resulting aqueous solution of the copolymer can be used either directly or the water can be distilled off to obtain a water-soluble powder.

In one process variant, the pyroglutamic acid melt is first cooled to about 120° C., and then the organofunctional polysiloxane is added. After some time the temperature is increased to 170° C. and only then is the aspartic acid added. This process variant has proven advantageous particularly for comb-like polysiloxanes.

The present invention also provides for the use of the polypeptide-polysiloxane copolymers in surface-active applications, in particular as silicone surfactants.

The polypeptide-polysiloxane copolymers according to the invention can be used in various applications. They are particularly suitable for use in aqueous media, where they exhibit their performance due to their interfacial activity and their affinity to surfaces. Depending on their structure, they can improve surface structure when used in plastics. They can also be used as oil-in-water or water-in-oil emulsifiers or as stabilizers in emulsions, or, for example, in cosmetic preparations for the cleansing of skin and hair, for improving foaming and for the conditioning of hair and/or for achieving a pleasant feel on the skin. As protein derivatives, they can be used as skin moisturizers or as agents for alleviating irritation of the skin. The polypeptide-polysiloxane copolymers according to the invention are of course frequently used together with surfactants and other additives for influencing surface quality. All said formulations can comprise known additives, such as, for example, wetting agents, surfactants or emulsifiers from the classes of anionic, cationic, zwitterionic, amphoteric or nonionic surface-active substances, for example fatty alcohol sulfates, fatty alcohol ether sulfates, alkylsulfonates, alkylbenzenesulfonates, sulfosuccinic alkyl esters, quaternary ammonium salts, alkyl betaines, carboxamidoalkyl betaines, derivatives of monomeric saccharides and saccharides with high degrees of condensation, ethoxylated fatty alcohols, fatty acid alkanolamides or ethoxylated fatty acid esters, thickeners, such as, for example, kaolin, bentonite, fatty acids, higher fatty alcohols, starch, polyacrylic acid or derivatives thereof, cellulose derivatives, alginates, petroleum jelly or paraffin oil.

In addition, use of the compounds according to the invention as textile auxiliaries or as additives in paints and surface coatings is also possible.

The examples below illustrate the present invention.

EXAMPLES

Example 1

50 g of glutamic acid were heated at 180° C. for half an hour under a stream of nitrogen in a 250 ml three-necked flask fitted with an electric heating jacket, stirrer, dropping funnel and thermometer. The reaction apparatus was an open apparatus so that the water formed during the reaction was largely removed by the nitrogen stream. The temperature of the melt was then adjusted to 170° C., and 50 g of aspartic acid were added in portions over the course of half an hour. The temperature was maintained for a further half hour at 170° C., and then 66.5 g (40% by weight based on the total mixture) of an α,ω-terminal aminopropyldimethylpolydimethylsiloxane (X-22-161 AS from Shin Etsu) were added dropwise over the course of half an hour. The mixture was then heated at 170° C. for another hour. The melt was poured while still hot into a mortar. After the melt had solidified to a glass-like mass, it was ground as finely as possible. The yellow powder was stirred for 12 hours in 1.5 l of water, the insoluble residue was filtered off and the residue was washed with water and ethanol and then dried in a drying cabinet at 60° C. to give 95 g (57% yield) of a yellow, water-insoluble powder. For NMR spectroscopic characterization, the product could be dissolved in [D6] dimethyl sulfoxide.

The yellow powder was first stirred with 1 l of 0.1 N sodium hydroxide solution, then with 630 ml of 1 N sodium hydroxide solution until an almost clear solution was formed. The mixture was neutralized with 3 N aqueous hydrochloric acid, and then the water was distilled off at 100° C. in an oil-pump vacuum to give a yellow powder which was soluble in water in any concentration.

Examples 2–5/Comparative Example

In Examples 2 to 5 the content of the aminosiloxane in the overall mixture in accordance with Example 1 was varied. The procedure remained the same. For comparison, an example not according to the present invention was used.

Example 2

11 g (10% by weight based on the total mixture) of aminopropyldimethylpolydimethylsiloxane (X-22-161 AS from Shin Etsu)

Example 3

25 g (20% by weight) of aminopropyldimethylpolydimethylsiloxane

Example 4

42.8 g (30% by weight) of aminopropyldimethylpolydimethylsiloxane

Example 5

100 g (50% by weight) of aminopropyldimethylpolydimethylsiloxane

Comparative Example 0 g (0% by weight) of aminopropyldimethylpolydimethylsiloxane

Example 6

50 g of glutamic acid were heated at 180° C. for half an hour under a stream of nitrogen in a 250 ml three-necked flask fitted with an electric heating jacket, stirrer, dropping funnel and thermometer. The reaction apparatus was an open apparatus so that the water formed during the reaction was largely removed by the nitrogen stream. The temperature of the melt was then adjusted to 170° C., and 75 g of a mixture of aspartic acid and cysteine (2:1) were added in portions over the course of half an hour. The temperature was maintained for a further half hour at 170° C., and then 83 g (40% by weight based on the total mixture) of an α,ω-terminal aminopropyldimethylpolydimethylsiloxane (X-22-161 AS from Shin Etsu) were added dropwise over the course of half an hour. The mixture was then heated at 170° C. for another hour. The melt was poured while still hot into a mortar. After the melt had solidified to a glass-like mass, it was ground as finely as possible. The yellow powder was stirred for 12 hours in 1.5 l of water, the insoluble residue was filtered off and the residue was washed with water and ethanol and then dried in a drying cabinet at 60° C. to give 129 g (62% yield) of a yellow, water-insoluble powder. For NMR spectroscopic characterization, the product was dissolved in [D6] dimethyl sulfoxide.

The yellow powder was first stirred with 1 l of 0.1 N sodium hydroxide solution, then with 900 ml of 1 N sodium hydroxide solution until an almost clear solution was formed. The mixture was neutralized with 3 N aqueous hydrochloric acid, and then the water was distilled off at 100° C. in an oil-pump vacuum to give a yellow powder which was soluble in water in any concentration. The sulfur content was determined as 1.1%.

Example 7

50 g of glutamic acid were heated at 180° C. for half an hour under a stream of nitrogen in a 250 ml three-necked flask fitted with an electric heating jacket, stirrer, dropping funnel and thermometer. The reaction apparatus was an open apparatus so that the water formed during the reaction was largely removed by the nitrogen stream. The melt was cooled to 120° C., and 66.5 g (40% by weight based on the total mixture) of an α,ω-terminal epoxy-functional polydimethylsiloxane (DMS-E12 from Gelest) were added dropwise over the course of half an hour. The mixture was heated at 150° C. for a further hour, then the temperature was increased to 170° C., and then 50 g of aspartic acid were added over the course of half an hour. After 1 h at 170° C., the mixture was cooled to 100° C., 83 g of 1 N sodium hydroxide solution were added, and the mixture was left to cool further with stirring. Solid sodium hydroxide was added until the solid had dissolved. If the pH of the aqueous solution was alkaline, 3 N aqueous hydrochloric acid was then used for neutralization. Most of the water was distilled off in an oil-pump vacuum, and the yellow and somewhat tacky mass was then dried at 60° C. in a drying cabinet to give a yellow powder, whose 1% strength aqueous solution was opaque and foamed very well.

Example 8

50 g of glutamic acid were heated at 180° C. for half an hour under a stream of nitrogen in a 250 ml three-necked flask fitted with an electric heating jacket, stirrer, dropping funnel and thermometer. The reaction apparatus was an open apparatus so that the water formed during the reaction was largely removed by the nitrogen stream. The melt was cooled to 120° C., and 11.1 g (10% by weight based on the total mixture) of a comb-like aminopropylpolydimethylsiloxane (3.8% nitrogen) were added dropwise over the course of half an hour. The mixture was heated to 170° C., and then 50 g of aspartic acid were added over the course of half an hour. After 1 h at 170° C., the melt, which was still hot, was poured into a mortar. After the melt had solidified to a glass-like mass, it was ground as finely as possible. The yellow powder (61 g) was stirred firstly with 1 l of 0.1 N sodium hydroxide solution, then with 400 ml of 1 N sodium hydroxide solution until an almost clear solution was formed. The mixture was neutralized with 3 N aqueous hydrochloric acid, and then the water was distilled off at 100° C. in an oil-pump vacuum to give a yellow powder, whose 1% strength aqueous solution was opaque and foamed well.

Performance

A) Physical Properties

Content of silicon in the compounds from Examples 2–6:

| Compound from Example | Abbreviation[1] | Silicon content [%] | Surface tension (0.1% in water) [mN/m] |
|---|---|---|---|
| 2 | Si-Pep (10% A-Si) | 3 | n.d. |
| 3 | Si-Pep (20% A-Si) | 6 | n.d. |
| 4 | Si-Pep (30% A-Si) | 8 | 32.6 |
| 5 | Si-Pep (50% A-Si) | 12 | n.d. |
| Comp. Example | | <0.01 | 57.5[2] | n.b. = not determined
[1] Si-Pep = silicone peptide; A-Si = amino-functional siloxane
[2] For comparison: The surface tension of pure water is 72 mN/m.

The table illustrates how the silicone content in the polypeptide-polysiloxane copolymer can be adjusted in a targeted manner by means of the amount of amino-functional siloxane used. In addition, the table shows, using compound 4 as an example, that the silicone peptides are interface-active since they clearly reduce the surface tension of water (72 mN/m). Although a thermal protein does also display interfacial activity, it is not very pronounced.

B) Sensory Test on Small Tresses of Hair

A test was carried out on small tresses of hair using the compounds from Examples 2–5 on bundles of Euro hair weighing 2 g of predamaged in a standardized manner. For this purpose, the hair was treated in the standardized way with an aqueous shampoo formulation which, in addition to 9% sodium lauryl ether sulfate and 3% of cocoamidopropylbetaine, comprised 1% (active content) of conditioners. The solutions were further thickened with sodium chloride, and the pH was adjusted to about 5.5. For comparison, a protein-silicone copolymer known in the market (Crodasone® W; EP-A-0 540 357) and a blank (without conditioner=placebo) were used. The sensory test was carried out by six selected subjects as a ranking test, within which a differentiation is inevitably obtained.

The small tresses of hair are assessed for their dry properties (dry combability, dry feel and shine) and wet properties (detangling, wet combability, wet feel). The results are given in Tables 1 and 2.

For "dry combability", the difference compared with placebo and commercial product is significant, and even a gradation toward falling silicone content can be detected. For "dry feel" no difference is possible, and for "shine" the results are scattered. It is notable that the commercial product is not better than the plaecbo.

In the case of the wet properties, for "detangling" and for "wet combability", the product based on 30% of aminosiloxane predominates; for "wet combability", the product based on 50% of aminosiloxane was also assessed as good. For "wet feel" all four products performed well. In the case of the wet properties a difference compared with the placebo can be detected.

In summary it is established that the conditioning properties of the silicone peptides from the Examples 2 to 5 according to the invention, particularly in the case of the dry properties, are significant. The products with higher contents of silicone are the best. The commercial product, on the other hand did not exhibit conditioning properties.

TABLE 1

Test on small tresses of hair: dry properties

| Product | Dry combability[1] | Dry feel[1] | Shine[1] |
|---|---|---|---|
| Si-Pep (10% A-Si) | 44 | 63 | 69 |
| Si-Pep (20% A-Si) | 63 | 58 | 43 |
| Si-Pep (30% A-Si) | 69 | 58 | 58 |
| Si-Pep (50% A-Si) | 72 | 58 | 75 |
| Crodasone W | 50 | 55 | 43 |
| Placebo | 50 | 55 | 58 |

[1] In each case as ranking total in %

TABLE 2

Test on small tresses of hair: wet properties

| Product | Detangling[1] | Wet combability[1] | Wet feel[1] |
|---|---|---|---|
| Si-Pep (10% A-Si) | 63 | 63 | 69 |
| Si-Pep (20% A-Si) | 61 | 41 | 67 |
| Si-Pep (30% A-Si) | 83 | 78 | 52 |

TABLE 2-continued

Test on small tresses of hair: wet properties

| Product | Detangling[1] | Wet combability[1] | Wet feel[1] |
|---|---|---|---|
| Si-Pep (50% A-Si) | 52 | 69 | 67 |
| Crodasone W | 36 | 39 | 41 |
| Placebo | 52 | 59 | 52 |

[1]In each case as ranking total in %

The above descriptions intended to be illustrative and not limiting. Various changes or modifications in the embodiments described may occur to those skilled in the art. These can be made without departing from the scope and spirit of the invention.

What we claim is:

1. A polypeptide-polysiloxane copolymer comprising:

a) at least one polysiloxane unit

[siloxane]—(sp)$_m$— where the index m is a positive integer in the range m=1–52, and

[siloxane]—(sp)$_{m-1}$— is of the general average formula I:

$$R_2-Si(R_1)(R_1)-O-[Si(R_1)(R_1)-O]_a-[Si(R_1)(sp)-O]_b-Si(R_1)(R_1)-R_2 \quad (I)$$

where
$R_1$ = alkyl radical,
$R_2$ = $R_1$ and/or -sp-
where
-sp- is divalent spacer between siloxane and another functional group, where the silicon atom and spacer are linked via a silicon-carbon bond, and the divalent alkylene radical has from 1 to 20 carbon atoms, which is optionally branched and optionally contains double bonds, aromatic rings, or heteroatoms, the indices a and b are integers in the ranges a=0–200 and b=0–50, with the proviso that when a=b=0 and when b=0 and a≠0, at least one $R_2$=-sp- in each case, and b) at least one polypeptide unit —C(O)—[therm. protein]—NH— where therm. protein is a structure of the general average formula II:

—C(O)—CH(R_3)—[NH—C(O)—CH(R_4)]_c—[NH—C(O)—CH(R_5)]_d—[N(—C(O)—CH_2—)—C(O)—CH—]_e—NH—

C-terminal end        N-terminal end or of the formula III:

(III)

—C(O)—CH(R_3)—[NH—C(O)—CH(R_4)]_c—[NH—C(O)—CH(R_5)]_d—[NH—C(O)—CH(CH_2—C(OH)(HO—)=O)]_f—NH—

C-terminal end        N-terminal end which is linked to the polysiloxane unit via a divalent functional group

-FGeither via the C-terminal end, the N-terminal end or both ends of the polypeptide unit, and which is a structural unit selected from the group consisting of:
—CH(OH)CH$_2$—, —CH(OH)CH$_2$O—, —CO—, —CH(CH$_2$CO$_2$H)CO—, —NH—, —O—, —S—, —CH(NH$_2$)CO— and —CH(CO$_2$H)NH— and optionally provides additional links between polysiloxane and polypeptide units via the radicals $R_4$ and/or $R_5$
where
$R_3$ = $R_4$ or $R_5$,
where
$R_4$ = is identical to a residue of an amino acid and —(CH$_2$)$_4$—NH—R$_6$,
where
$R_6$ = H (lysine) or —FG—sp—[siloxane]—(sp)$_{m-1}$ $R_5$ = —CH$_2$—CH$_2$—CO—R$_6$
where
$R_6$ = OH (glutamic acid) or —FG—sp—[siloxane]—(sp)$_{m-1}$ c, d, e and f are positive integers including 0,
with the proviso that
the indices c, d, e in formula II and c, d and f in formula III are not all 0, and
the molecular weight of the polypeptide unit is between 250 and 9000 and the weight ratio of polysiloxane units and polypeptide units in the polypeptide-polysiloxane copolymer is between 1:99 and 99:1.

2. The polypeptide-polysiloxane copolymer as claimed in claim 1, wherein
$R_1$ is a $C_1$–$C_4$ alkyl group
-sp- is a divalent spacer between siloxane and another functional group, where the silicon atom and spacer are linked via a silicon-carbon bond, and the divalent alkylene radical has from 1 to 20 carbon atoms, which is optionally branched and optionally contains double bonds, aromatic rings, or heteroatoms selected from the group consisting of oxygen, nitrogen or sulfur, and the molecular weight of the polypeptide unit is between 250 and 9000 and the weight ratio of polysiloxane units and polypeptide units in the polypeptide-polysiloxane copolymer is between 1:99 and 99:1.

3. The polypeptide-polysiloxane copolymer as claimed in claim 1, wherein $R_1=CH_3$, m=2–32, a=8–100, b=0–30, where, when b=0 both radicals $R_2$ then correspond to -sp-.

4. The polypeptide-polysiloxane copolymer as claimed in claim 1, wherein m=2–17, a=8–40, b=0–15, where, when b=0, both radicals $R_2$ then correspond to -sp-.

5. The polypeptide-polysiloxane copolymer as claimed in claim 1, wherein c, d and e in formula II or c, d and f in formula III≠0, where the weight ratio of polysiloxane units and polypeptide units in the polypeptide-polysiloxane copolymer is between 5:95 and 55:45.

6. The polypeptide-polysiloxane copolymer as claimed in claim 1, wherein c in formula II or formula III=0 and d and e in formula II or d and f in formula III≠0 and $R_3=R_5$ or —$CH_2$—CO—$R_6$
where
$R_6$=OH (aspartic acid) or

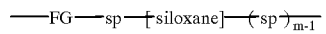

and the weight ratio of polysiloxane units and polypeptide units in the polypeptide-polysiloxane copolymer is between 5:95 and 55:45.

7. The polypeptide-polysiloxane copolymer as claimed in claim 1, wherein c and d in formula II or formula III=0, and e or f in formula II or formula III≠0 and $R_3$=—$CH_2$—CO—$R_6$
where
$R_6$=OH (aspartic acid) or

and the weight ratio of polysiloxane units and polypeptide units in the polypeptide-polysiloxane copolymer is between 5:95 and 55:45.

8. The polypeptide-polysiloxane copolymer as claimed in claim 1, wherein
-sp- is selected from the group consisting of

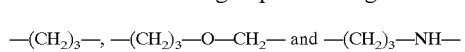

and
-FG- is selected from the group consisting of

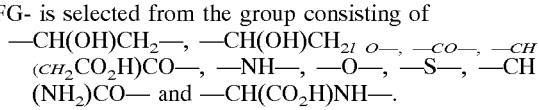

9. The polypeptide-polysiloxane copolymer as claimed in claim 1, wherein -sp- is selected from the group consisting of

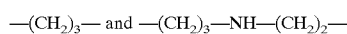
and
-FG- is —NH—.

10. The polypeptide-polysiloxane copolymer as claimed in claim 1, wherein the amino acid is selected from the group consisting of glycine, alanine, valine, leucine, isoleucine, phenylalanine, proline, serine, threonine, tyrosine, asparagine, glutamine, arginine, tryptophan, histidine, cysteine, methionine, aspartic acid and glutamic acid.

11. A process for the preparation of polypeptide-polysiloxane copolymers as claimed in claim 1 by thermal polymerization of amino acids of the general formula:

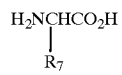

where $R_7$ is identical or different and is the radical of an amino acid, in the presence of organopolysiloxanes having reactive groups

-RGof the general average formula (I')

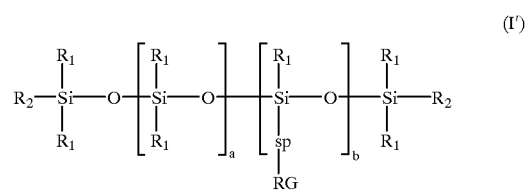

with the proviso that on average at least one residue -sp- RG is present, wherein the RG is chosen from epoxy, carboxy, amino, thio, amino acid or hydroxyl groups and, optionally, further hydrolyzing the succinimide units in the polypeptide to aspartic acid units by alkaline hydrolysis.

12. The process as claimed in claim 11, where the amino acid is glycine, alanine, valine, leucine, isoleucine, phenylalanine, proline, serine, threonine, tyrosine, asparagine, glutamine, arginine, lysine, tryptophan histidine, cysteine, methionine, aspartic acid, glutamic acid or a mixture of one or more of these amino acids.

13. The process as claimed in claim 11 wherein b is 0 in formula I' and at least one of the two radicals $R_2$ correspond to the residue -sp-RG.

14. The process as claimed in claim 11, wherein the amino acid is a mixture of the amino acids aspartic acid, glutamic acid and one or more other amino acids.

15. The process as claimed in claim 11, which the amino acid is a mixture of the amino acids aspartic acid and glutamic acid.

16. The process as claimed in claim 11, wherein the amino acid is aspartic acid.

17. The process as claimed claim 11, wherein the weight ratio of aspartic acid to glutamic acid is between about 5:1 and about 1:5, and the content of other amino acids in the mixture is from 0 to about 30% by weight.

* * * * *